United States Patent
Abe et al.

(10) Patent No.: US 9,161,737 B2
(45) Date of Patent: Oct. 20, 2015

(54) ULTRASONIC DIAGNOSTIC APPARATUS AND ULTRASONIC IMAGE PROCESSING APPARATUS

(75) Inventors: Yasuhiko Abe, Otawara (JP); Tetsuya Kawagishi, Nasushiobara (JP)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 228 days.

(21) Appl. No.: 13/167,282

(22) Filed: Jun. 23, 2011

(65) Prior Publication Data

US 2011/0319761 A1 Dec. 29, 2011

(30) Foreign Application Priority Data

Jun. 25, 2010 (JP) ................. 2010-145519

(51) Int. Cl.
*A61B 8/00* (2006.01)
*A61B 8/08* (2006.01)

(52) U.S. Cl.
CPC ............... *A61B 8/0883* (2013.01); *A61B 8/485* (2013.01)

(58) Field of Classification Search
CPC .................................................. A61B 8/0883
See application file for complete search history.

(56) References Cited

U.S. PATENT DOCUMENTS

| | | | |
|---|---|---|---|
| 5,938,606 | A | 8/1999 | Bonnefous |
| 7,824,337 | B2 | 11/2010 | Abe et al. |
| 2004/0116810 | A1 | 6/2004 | Olstad |
| 2010/0056919 | A1* | 3/2010 | Abe .............................. 600/443 |

FOREIGN PATENT DOCUMENTS

| | | |
|---|---|---|
| CN | 1774646 A | 5/2006 |
| CN | 101361665 A | 2/2009 |
| CN | 101647717 A | 2/2010 |
| CN | 101732036 A | 6/2010 |
| JP | 09-313486 A | 12/1997 |
| JP | 3187088 A | 10/1998 |
| JP | 2004-173589 A | 6/2004 |

(Continued)

OTHER PUBLICATIONS

CN Office Action with English Translation for CN Application No. 201110172637.5 mailed on Jan. 5, 2013.

(Continued)

*Primary Examiner* — Mark Remaly
(74) *Attorney, Agent, or Firm* — Yoshida & Associates, LLC

(57) ABSTRACT

According to one embodiment, an ultrasonic diagnostic apparatus comprises a data acquisition unit configured to scan a region which includes at least part of a heart of an object and acquire ultrasonic data associated with the region, a curve acquisition unit configured to acquire temporal change curves of a wall motion parameter associated with a plurality of regions of the heart by using the ultrasonic data associated with the region to be scanned and a value acquisition unit configured to acquire an index value associated with cardiac wall motion by calculating a difference value of the wall motion parameter of two arbitrary regions, of the plurality of regions of the heart, at each phase in an analysis period by using temporal change curves associated with the two arbitrary regions, calculating a total sum of the difference values in the analysis period, and normalizing the total sum with a predetermined value.

18 Claims, 8 Drawing Sheets

(56) References Cited

FOREIGN PATENT DOCUMENTS

| | | |
|---|---|---|
| JP | 2005-073788 A | 3/2005 |
| WO | 03/015635 A1 | 2/2003 |

OTHER PUBLICATIONS

Japanese Office Action with its English translation for Japanese Patent Application No. 2010-145519 mailed on Jan. 7, 2014.

* cited by examiner

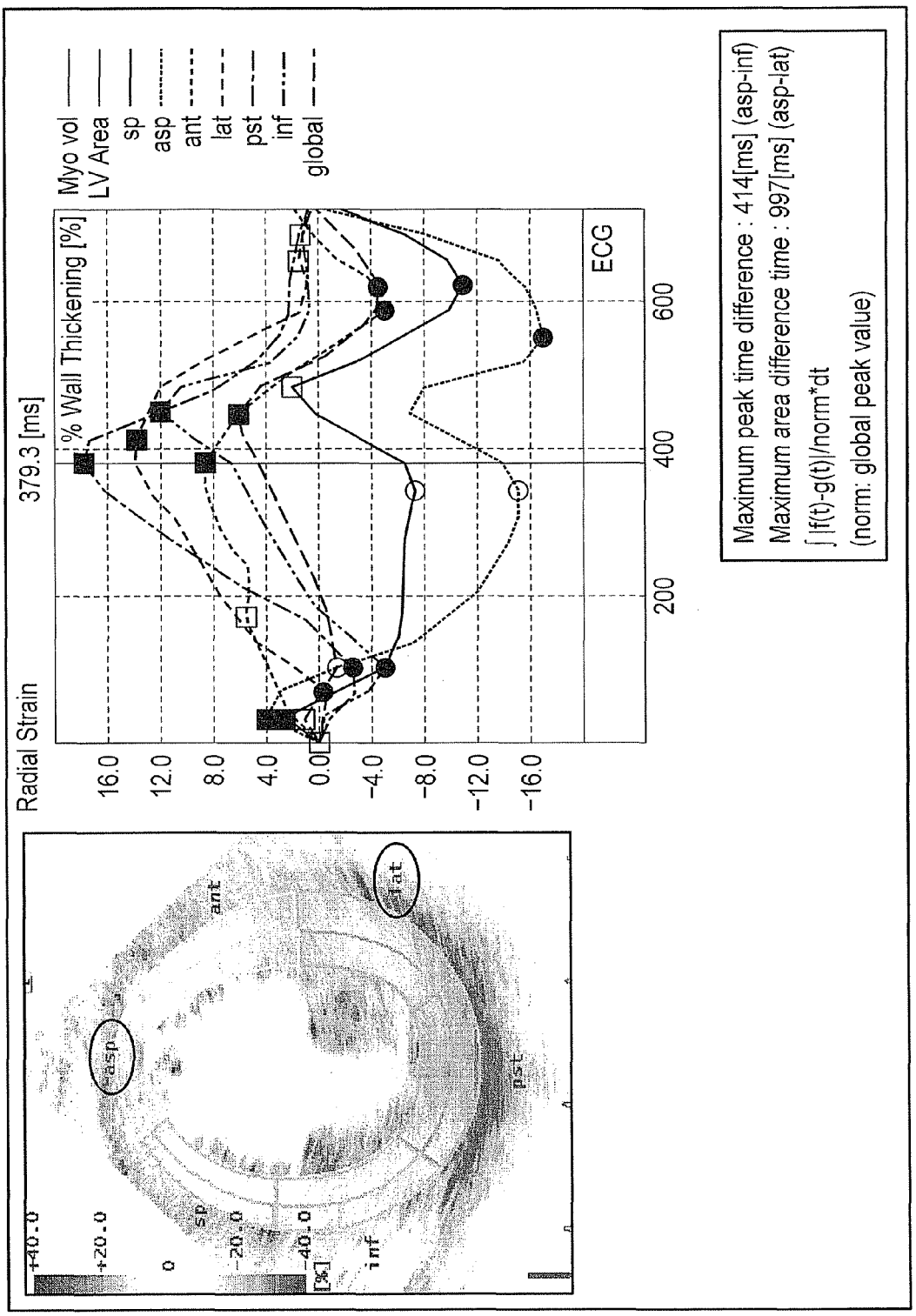
F I G. 4

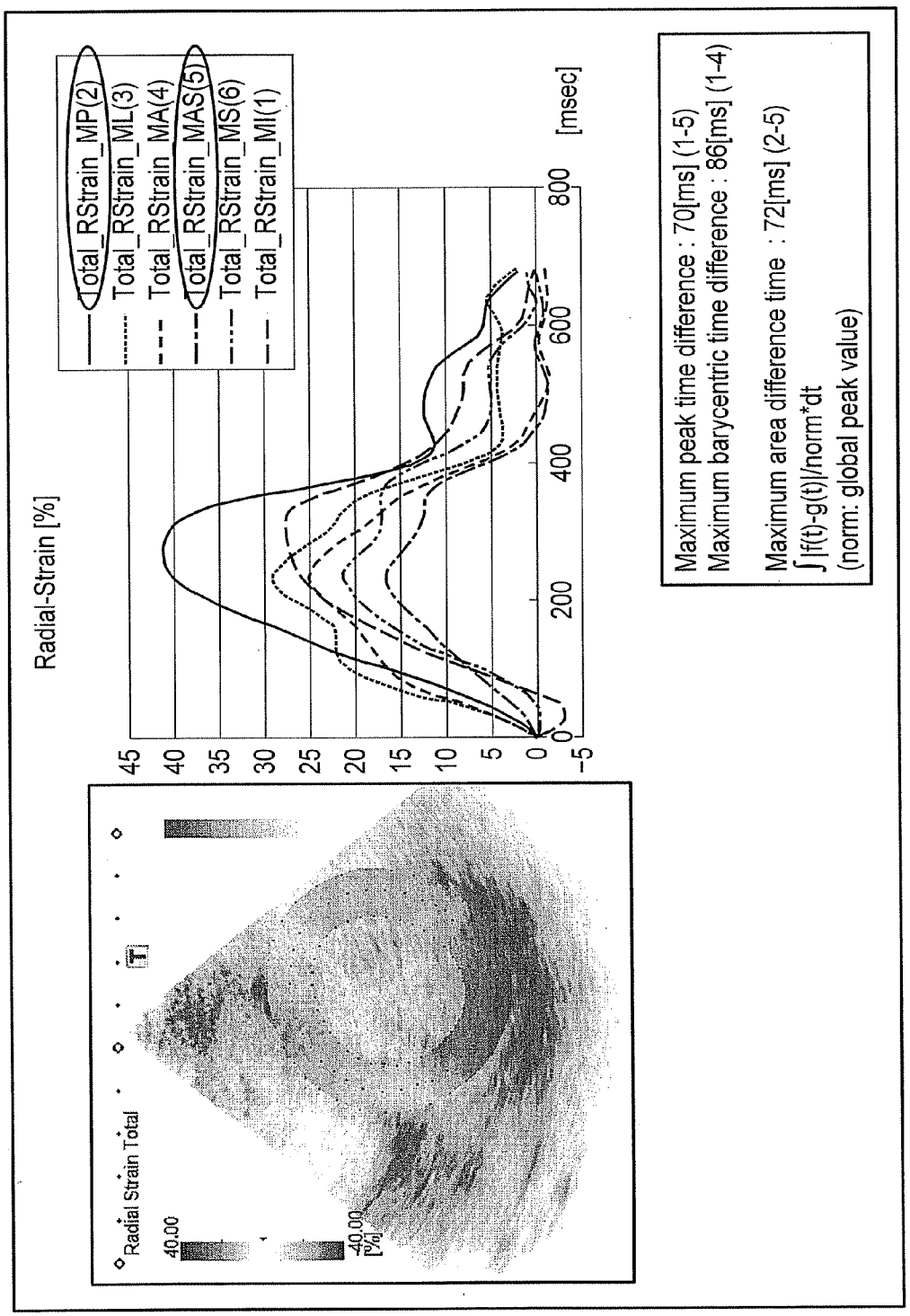
F I G. 5

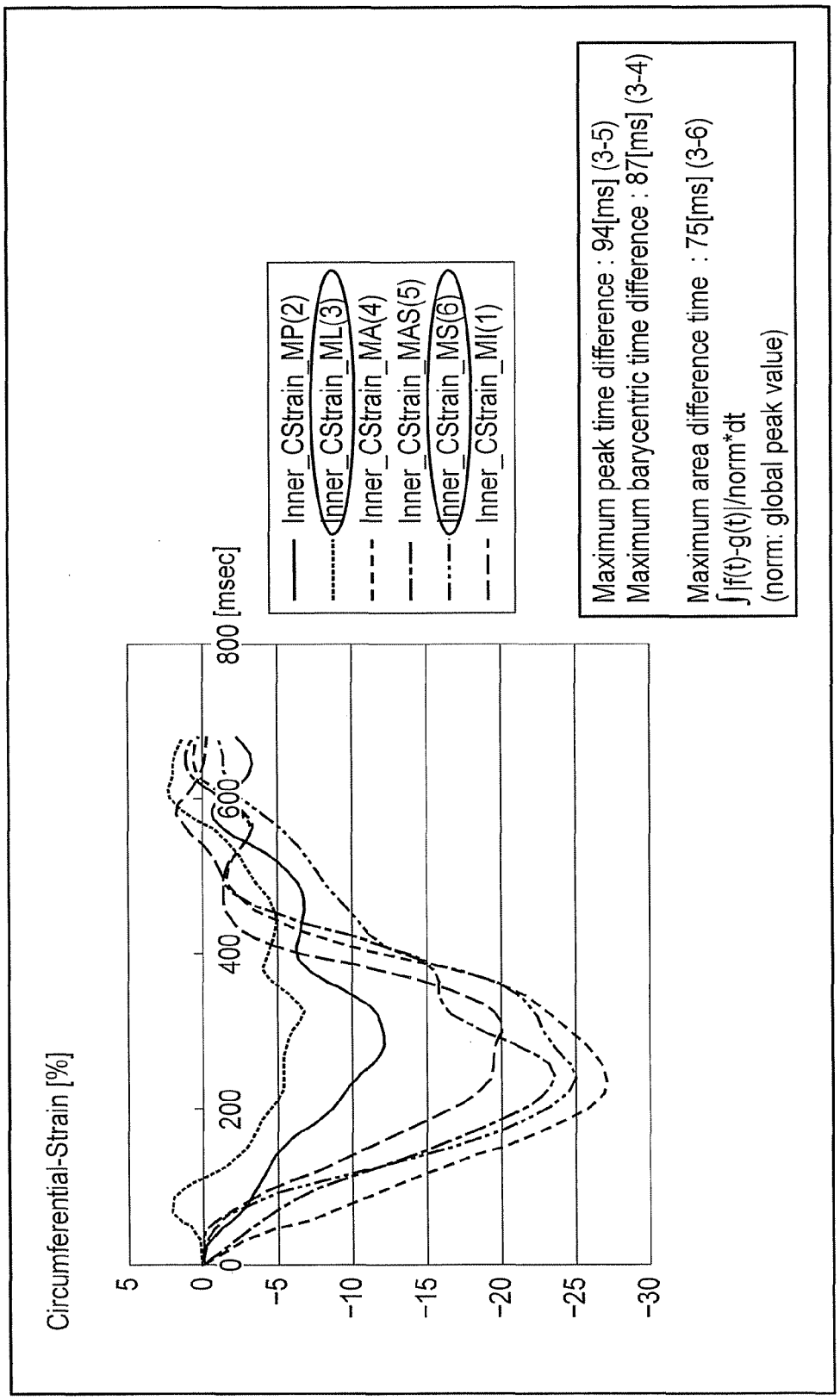
F I G. 6

ULTRASONIC DIAGNOSTIC APPARATUS AND ULTRASONIC IMAGE PROCESSING APPARATUS

CROSS-REFERENCE TO RELATED APPLICATIONS

This application is based upon and claims the benefit of priority from Japanese Patent Application No. 2010-145519, filed Jun. 25, 2010; the entire contents of which are incorporated herein by reference.

FIELD

Embodiments described herein relate generally to an ultrasonic diagnostic apparatus and an ultrasonic image processing apparatus.

BACKGROUND

With regard to a living tissue such as cardiac muscle, it is very important for the diagnosis of the tissue to objectively and quantitatively evaluate its function. For example, much attention has recently been paid to cardiac resynchronization therapy (CRT) for severe heart failure patients, and much importance has been attached to quantitative evaluation with echocardiography for prior determination for application to CRT and treatment effect determination. CRT is a therapy which can improve the dyssynchrony of cardiac wall motion which tends to coexist in severe heart failure patients. Patients (responders) for whom this therapy is effective have shown dramatic symptomatic improvements. On the other hand, the problem is that patients (non responders) with heart failure cases for whom CRT is not effective occupy as much as about 30% of the patients at the year of 2005.

Non responders are heart failure patients who are not suffering from dyssynchrony. In the past, the application of CRT has been determined with criteria of QRS width >130 msec and ejection fraction (EF)≤35% on electrocardiograms. With these criteria, however, even heart failure patients who are not suffering from dyssynchrony, i.e., non responders, are also included.

Under the circumstances, worldwide attempts have begun to be made to extract only dyssynchrony symptoms by quantitative evaluation methods using echocardiography, and there have been proposed various techniques using velocity arrival time imaging, displacement or strain arrival time (peak time or barycentric time) imaging, and the like. Each of these techniques aims at outputting differences in contraction timing among local cardiac muscles as a color image and allowing easy comprehension of the presence/absence of dyssynchrony and regions with abnormal contraction timings. In this case, "peak time differences of temporal changes associated with a cardiac wall motion parameter" such as velocity, displacement, or strain are most commonly used as contraction timing differences.

It is, however, reported in the PROSPECT study (Circulation. 2008; 117:2608-16) result that using an index in an echocardiographic Doppler method such as velocity or displacement, i.e., a peak time difference, cannot significantly distinguish between a responder and a non responder.

On the other hand, a technique for dissynchrony evaluation using barycentric times as well as peak times has also been proposed. That is, the use of a barycentric time has been proposed in consideration of the fact that stable dissynchrony evaluation cannot be performed by using only a peak when even slight noise mixes in near a peak phase of velocity or displacement or cannot be performed when a plurality of peaks exist. However, even when using a barycentric time, like when using the above peak time difference, some restriction is imposed on the detection of dissynchrony (abnormality) effective for the application of CRT. In addition, since a temporal difference in barycentric time between normality and abnormality is generally smaller than that in peak time, it is difficult to distinguish between normality and abnormality.

Therefore, conventional indices associated with dissynchrony cannot significantly distinguish between responders and non responders for CRT.

BRIEF DESCRIPTION OF THE DRAWINGS

FIG. 4 is a view showing an example of how this dissynchrony evaluation support function is applied to a case of left bundle branch block for which CRT is effective;

FIG. 5 is a view showing an example of how this dissynchrony evaluation support function is applied to a normal case;

FIG. 6 is a view showing an example of how this dissynchrony evaluation support function is applied to a normal case;

DETAILED DESCRIPTION

Figure 1:
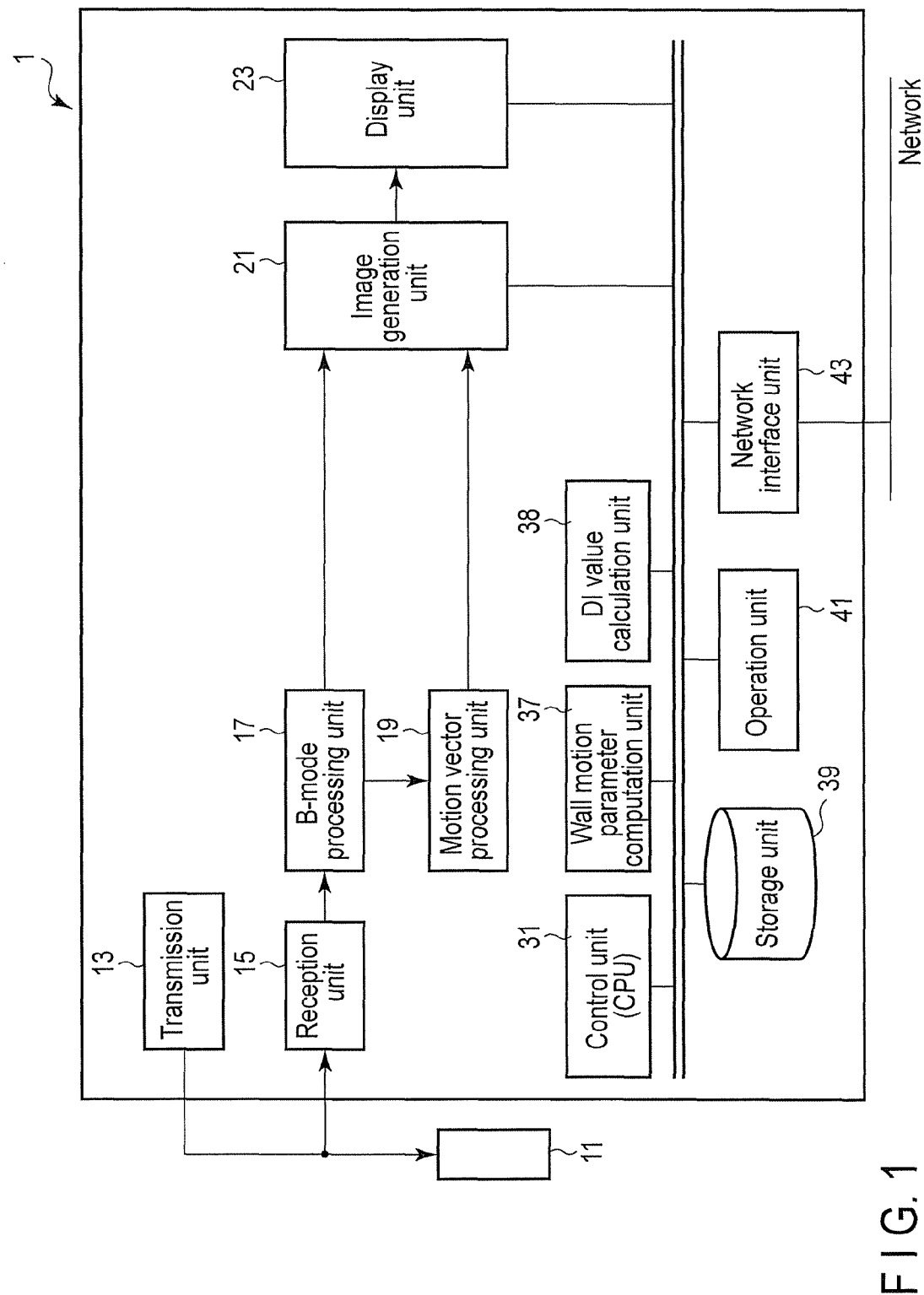
FIG. 1 is a block diagram showing the arrangement of an ultrasonic diagnostic apparatus 1 according to an embodiment.

In general, according to one embodiment, an ultrasonic diagnostic apparatus comprises a data acquisition unit configured to ultrasonically scan a two-dimensional region or a three-dimensional region as a region to be scanned which includes at least part of a heart of an object and acquire ultrasonic data associated with the region to be scanned, a temporal change curve acquisition unit configured to acquire temporal change curves of a wall motion parameter associated with a plurality of regions of the heart by using the ultrasonic data associated with the region to be scanned, an index value acquisition unit configured to acquire an index value associated with cardiac wall motion by calculating a difference value of the wall motion parameter of two arbitrary regions, of the plurality of regions of the heart, at each phase in an analysis period by using temporal change curves associated with the two arbitrary regions, calculating a total sum of the difference values in the analysis period, and normalizing the total sum with a predetermined value, and a display unit configured to display the index value in a predetermined form.

The first and second embodiments will be described below with reference to the views of the accompanying drawing. Note that the same reference numerals in the following description denote constituent elements having almost the same functions and arrangements, and a repetitive description will be made only when required.

Note that each embodiments described below will exemplify a case wherein the present embodiment is applied to an ultrasonic diagnostic apparatus. However, the present embodiments are not limited to this, and can be applied to an ultrasonic image processing apparatus such as a workstation or personal computer.

(First Embodiment)

FIG. 1 is a block diagram showing the arrangement of an ultrasonic diagnostic apparatus 1 according to the first embodiment. The ultrasonic diagnostic apparatus 1 includes an ultrasonic probe 11, a transmission unit 13, a reception unit 15, a B-mode processing unit 17, a motion vector processing unit 19, an image generation unit 21, a display unit 23, a control unit (CPU) 31, a wall motion parameter computation unit 37, a DI (Discoordination Index) value calculation unit 38, a storage unit 39, an operation unit 41, and a network interface unit 43. Note that when this embodiment is applied to an ultrasonic image processing apparatus, the units enclosed by the dotted line in FIG. 1 are the constituent elements of the apparatus.

The ultrasonic probe 11 includes a plurality of piezoelectric transducers which generate ultrasonic waves based on driving signals from the transmission unit 13 and convert reflected waves from an object into electrical signals, a matching layer provided for the piezoelectric transducers, and a backing member which prevents ultrasonic waves from propagating backward from the piezoelectric transducers. When the ultrasonic probe 11 transmits ultrasonic waves to an object, various harmonic components are generated due to the nonlinearity of a living tissue upon propagation of ultrasonic waves. Fundamental waves and harmonic components constituting transmission ultrasonic waves are scattered backward by acoustic impedance boundaries of the tissue in the living body, micro-scattering, and the like, and are received as reflected waves (echoes) by the ultrasonic probe 11.

The transmission unit 13 includes a delay circuit and pulser circuit which are not shown. The pulser circuit repetitively generates rate pulses for the formation of transmission ultrasonic waves at a predetermined rate frequency fr Hz (period: 1/fr sec). The delay circuit gives each rate pulse a delay time necessary to focus an ultrasonic wave into a beam and determine transmission directivity for each channel. The transmission unit 13 applies a driving pulse to each transducer so as to form an ultrasonic beam toward a predetermined scan line at the timing based on this rate pulse.

The reception unit 15 includes an amplifier circuit, A/D converter, and adder (not shown). The amplifier circuit amplifies an echo signal received through the probe 11 for each channel. The A/D converter gives the amplified echo signals delay times necessary to determine reception directivities. The adder then performs addition processing for the signals. With this addition, an ultrasonic echo signal corresponding to a predetermined scan line is generated.

The B-mode processing unit 17 performs envelope detection processing for the ultrasonic echo signal received from the reception unit 15 to generate a B-mode signal corresponding to the amplitude intensity of the ultrasonic echo.

The motion vector processing unit 19 detects the movement position of each tissue by using pattern matching processing between two ultrasonic data in different phases, and obtains the displacement amount (or velocity) of the tissue based on the movement position. More specifically, with regard to a region of interest in one ultrasonic data, the motion vector processing unit 19 obtains a corresponding region in the other ultrasonic data which exhibits the highest similarity. Obtaining the distance between the region of interest and the corresponding region can obtain the displacement amount of the tissue. In addition, dividing this displacement amount by the time difference between the ultrasonic data (frame rate or volume rate) can obtain the moving velocity of the tissue. Performing this processing at each position on the ultrasonic data can acquire the displacement (motion vector) of each tissue or spatial-temporal distribution data associated with the displacements of the tissues. Note that ultrasonic data is defined as a set of reception signals having two-dimensional or three-dimensional positional information (i.e., a set of reception signals having spatial information).

The image generation unit 21 generates a B-mode ultrasonic image representing a two-dimensional distribution associated with a predetermined slice of the B-mode signal. In addition, based on the computed wall motion parameters, the image generation unit 21 also generates a two-dimensional or three-dimensional image in which the wall motion parameters are mapped by using a technique such as surface rendering or Polar-Mapping.

The display unit 23 displays an ultrasonic image, a wall motion parameter image in which the wall motion parameters are mapped at the respective corresponding positions, the temporal change curves of the wall motion parameters at the respective regions, and the like in predetermined forms, based on the video signal from the image generation unit 21. The display unit 23 also labels each region segmented by segmentation processing in accordance with the dissynchrony evaluation support function (to be described later), and displays the resultant image in a predetermined form.

The control unit (CPU) 31 has a function as an information processing apparatus (computer), and statically or dynamically controls the operation of the main body of this ultrasonic diagnostic apparatus. In particular, the control unit 31 implements the dissynchrony evaluation support function (to be described later) by expanding a dedicated program stored in the storage unit 39 in a memory (not shown).

The wall motion parameter computation unit 37 generates a wall motion parameter for each phase based on the spatial-temporal distribution data output from the motion vector processing unit 19. In this case, a wall motion parameter is physical information which can be acquired in association with of tissue motion, e.g., a displacement, strain, strain rate, velocity, torsion, or torsion rate in a predetermined direction of a predetermined tissue such as the cardiac wall.

The DI value calculation unit 38 calculates DI values to be used for dissynchrony evaluation in accordance with the dissynchrony evaluation support function (to be described later).

The storage unit 39 includes recording media such as magnetic disks (floppy® disks, hard disks, and the like), optical disks (CD-ROMs, DVDs, and the like), and semiconductor memories, and a device which reads information recorded in the media. The storage unit 39 stores transmission/reception conditions, a predetermined scan sequence, raw data and ultrasonic image data (e.g., tissue image data captured in the tissue Doppler mode, B mode, and the like) corresponding to each phase, ultrasonic data generated in advance for each phase, spatial-temporal distribution data associated with motion vectors, a program for implementing the dissynchrony evaluation support function (to be described later), diagnosis information (patient IDs, findings by doctors, and the like), a diagnostic protocol, a body mark generation program, and the like.

The operation unit 41 includes a mouse, trackball, mode switch, and keyboard which are connected to the apparatus main body to, for example, issue various instructions from the operator, an instruction to set a region of interest (ROI), and instructions to set various kinds of image quality conditions and select an arbitrary wall motion parameter in the dissynchrony evaluation support function (to be described later), an arbitrary analysis period, and a phase.

The network interface unit 43 is a device which transmits and receives information to and from other apparatuses via a network. It is possible to transfer, for example, data and analysis results such as ultrasonic images obtained by the ultrasonic diagnostic apparatus 1 to other apparatuses via a network by using the network interface unit 43.

(Theoretical Background)

It is pointed out that the dissynchrony of the cardiac wall motion of a type of patient (responder) for which CRT is effective exhibits a larger difference in wall motion parameter value between regions assuming that the peak time difference between the regions remains the same. For example, if local wall motion abnormality (akinesis) has occurred or the ventricular wall has become fibrotic due to cardiac infarction, a peak time difference in wall motion parameter tends to occur between the region and a healthy region. Even if pacing is applied to such a lesion by CRT, dyssynchrony occurs because of the lack of the remaining power of the cardiac muscles. As a result, this patient becomes a non responder. In this case, it is an essential problem that only the peak time difference does not clarify the degree of the difference in wall motion parameter value between the regions.

Figure 2A:
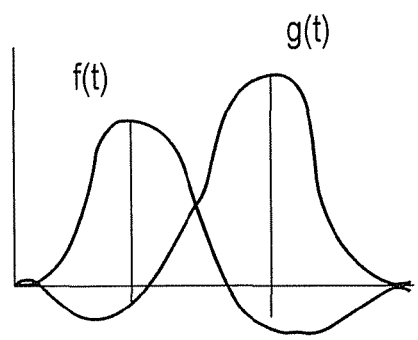
FIGS. 2A, 2B, 2C, and 2D are graphs showing four cases of temporal change curves f(t) and g(t) of wall motion parameters at two different regions.
Figure 2B:
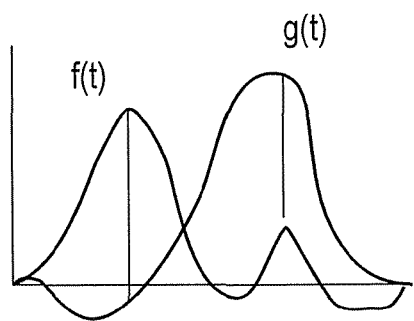
Figure 2C:
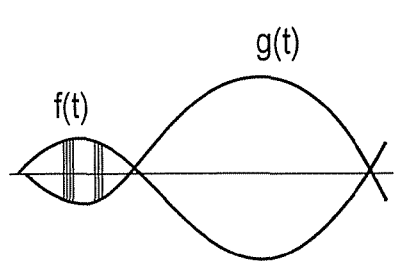
Figure 2D:
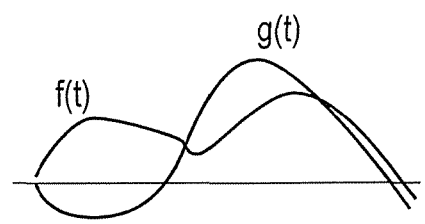

FIGS. 2A, 2B, 2C, and 2D are graphs showing four cases of temporal change curves f(t) and g(t) (e.g., strain waveforms) of wall motion parameters at two different regions (the ordinate representing the strain; and the abscissa, the time). Referring to FIGS. 2A, 2B, 2C, and 2D, for example, comparison between the case of FIG. 2A and the case of FIG. 2B indicates that although the peak time differences between the two regions in the two cases are the same, the dissynchrony in the case of FIG. 2A is higher than that in the case of FIG. 2B from the viewpoint of the effectiveness of CRT. That is, using only peak time differences cannot discriminate between the case of FIG. 2A for which CRT is relatively effective and the case of FIG. 2B. Likewise, comparison between the case of FIG. 2C and the case of FIG. 2D indicates that the dissynchrony in the case of FIG. 2C is higher than that in the case of FIG. 2D from the viewpoint of the effectiveness of CRT. In addition, note that in the case of FIG. 2C, the barycentric time differences between the two regions are the same, and hence using only barycentric times cannot detect dissynchrony.

Dissynchrony between two regions typified by a peak time difference and a barycentric time difference in the prior art is called the dyssynchrony of local cardiac muscle. On the other hand, the concept of dissynchrony in consideration of such difference in wall motion parameter value between regions is called the "discoordination of the left ventricle". It is thought that as the degree of the discoordination of the left ventricle increases, CRT becomes more effective. It is also thought that, from the point of view of temporal change curves, the difference in wall motion parameter value between regions corresponds to the area value (area difference value) of an area enclosed by two temporal change curves corresponding to the respective regions.

(Dissynchrony Evaluation Support Function)

The dissynchrony evaluation support function of the ultrasonic diagnostic apparatus 1 will be described next. This function introduces an index value for evaluating the performance of cardiac wall motion as a value quantitatively reflecting the discoordination of the left ventricle. As a typical value of this index value, a DI value is calculated by normalizing the area difference value between different two regions (e.g., two different segments obtained by dividing the cardiac wall by segmentation) with a predetermined value. Displaying such a DI value as dissynchrony evaluation support information in a predetermined form can support the evaluation of the dissynchrony of cardiac wall motion.

In the following description, a segment is synonymous with a local region. In addition, the following description will exemplify a case in which this dissynchrony evaluation support function is applied to a two-dimensional region including the left ventricle as a region to be scanned. However, this embodiment is not limited to this. For example, the dissynchrony evaluation support function can be applied to a three-dimensional region including the left ventricle as a region to be scanned.

Figure 3:
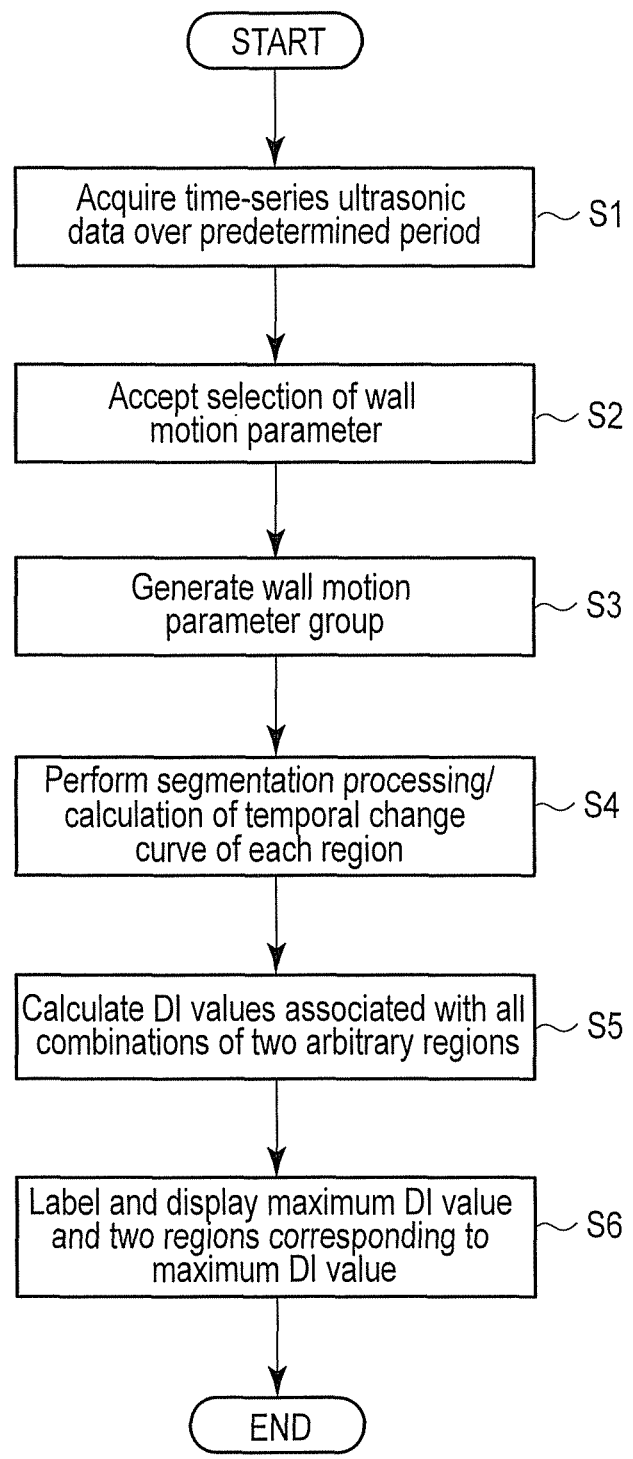
FIG. 3 is a flowchart showing a procedure for processing (dissynchrony evaluation support processing) based on an dissynchrony evaluation support function according to the first embodiment.

FIG. 3 is a flowchart showing a procedure for processing (dissynchrony evaluation support processing) based on the dissynchrony evaluation support function according to this embodiment. The contents of processing in each step in dissynchrony evaluation support processing will be described below with reference to FIG. 3.

[Acquisition of Time-Series Volume Data Group Over Predetermined Period: Step S1]

First of all, time-series ultrasonic data (to be referred to as a "time-series ultrasonic data group" hereinafter) over a predetermined period equal to or more than at least one heartbeat is acquired from a two-dimensional region including at least the left ventricle of an object as a region to be scanned (step S1).

[Acceptance of Selection of Wall Motion Parameter: Step S2]

The control unit 31 then accepts the selection of a wall motion parameter from the operator via the operation unit 41 (step S2). Assume that in this embodiment, for a concrete description, a strain is selected as a wall motion parameter in step S2. However, this embodiment is not limited to this, and it is possible to use, for example, a strain rate, displacement, or velocity as a wall motion parameter.

[Generation of Wall Motion Parameter Group: Step S2]

The motion vector processing unit 19 then extracts a cardiac muscle region from ultrasonic data, of ultrasonic data constituting the acquired time-series ultrasonic data group over the predetermined period and corresponding to the respective phases each corresponding to one heartbeat or more, which corresponds to a predetermined phase in accordance with an instruction from the user, and executes the speckle tracking processing of temporally tracking the extracted local cardiac muscle region by two-dimensional pattern matching processing, thereby computing spatiotemporal motion vector information. The wall motion parameter computation unit 37 also computes the wall motion parameter designated by the operator via the operation unit 41 using the computed spatiotemporal motion vector information, and generates a two-dimensional wall motion parameter group constituted by wall motion parameters corresponding to one heartbeat or more (step S3).

[Calculation of Segmentation Processing/Temporal Change Curves: Step S4]

The DI value calculation unit 38 segments a cardiac muscle region extracted from ultrasonic data corresponding to each phase into N local regions (segments) (segmentation processing), and calculates the temporal change curve of a wall motion parameter for each local region (step S4). Note that a number N of local regions is suitably about six when data to be segmented is two-dimensional data. When data to be segmented is volume data, the number N is suitably 16 according to ASE, and 17 according to AHA. In this embodiment, for a concrete description, N=6.

[Calculation of DI Values Associated with All Combinations: Step S5]

The DI value calculation unit 38 then calculates DI values associated with all the combinations of two different local regions (step S5). That is, the DI value calculation unit 38 calculates DI values associated with a wall motion parameter according to equation (1) when f(t) and g(t) respectively represent temporal change curves of two arbitrary local regions Si and Sj (where i≠j, and i and j are integers satisfying 1≤i and j≤6 (the numbers of segmentations)):

$$DI\ \text{value} = (\Sigma |f(t)-g(t)|/\text{norm}) \cdot dt \qquad (1)$$

where $\Sigma$ represents computation of a time sum in an analysis period (e.g., one cardiac cycle). Upon calculating DI values associated with all the combinations of two different local regions according to equation (1), the number of DI values obtained is $_N C_2/2$ (in this case, $_6 C_2/2=15$).

In equation (1), $\Sigma |f(t)-g(t)|$ represents the area difference value between the curves of the wall motion parameters f(t) and g(t) of the two different local regions. In addition, norm represents a normalization value required to absorb the influences of variations in the values of the temporal change curves of local regions (e.g., wall motion parameter values such as strain values have a significant difference between segments even in a normal case) and variations in curve absolute value due to disease states (for example, the absolute value of the wall motion parameter is relatively large in a normal case, but is small in a heart failure case or the like). It is preferable to use, as this normalization value, the peak value of the average curve (global) of overall N segments, which has the same unit as that of the numerator. Using this value will relatively reduce the weight for the DI value of a segment having a small parameter value relative to the overall parameter values, in addition to the above effects of normalization. In this case, another effect is that the influence of a region exhibiting a deterioration in wall motion to which CRT is difficult to respond does not easily reflect. Another normalization value is the peak value of f(t) or g(t). These values indicate that one of a pair of parameter values normalizes the other value. In addition, dt of equation (1) represents a predetermined time pitch. Multiplying the time pitch dt indicates that the magnitude of the area difference between the curves is converted into a time value (temporal integration). This term is not essential to the embodiment. However, converting the unit of a DI value into a time allows comparison with conventional peak values and the like.

Note that the normalization technique to be used is not limited to the above example. For example, it is possible to execute normalization by using a predetermined value which can be set for each wall motion parameter.

As a time interval (analysis period) that integrates the area difference given by equation (1), one cardiac cycle is preferably used, as described above, when a wall motion parameter is a physical quantity which becomes unimodal in a normal case, such as displacement or strain. In contrast to this, different analysis periods are preferably set for a systolic phase and a diastolic phase when a wall motion parameter is a physical quantity which has peaks with different polarities in a systolic phase and a diastolic phase in a normal case such as velocity or strain rate.

[Labeling/Display of Regions Corresponding to Maximum DI Value and DI Values: Step S6]

The DI value calculation unit 38 decides the maximum DI value (representative value) among the calculated DI values associated with all the combinations. The display unit 23 displays a wall motion parameter image which labels at least one, preferably both, of two local regions corresponding to the decided maximum DI value, and temporal change curves, together with the maximum DI value, for dissynchrony evaluation support, in predetermined forms (step S6). Note that a representative value is not limited to the maximum DI value, and may be another predetermined statistical value.

Several application examples of this dissynchrony evaluation support function will be described below. In each example, DI values are calculated from a two-dimensional short-axis image by using strain as a wall motion parameter obtained by a two-dimensional speckle tracking technique. As a norm in calculation of DI values, the peak value of the average curve of all N segments. In each of these application examples, segments 1 to 6 respectively correspond to anatomical regions (local regions obtained by segmentation) in a short-axis image of the heart as follows: 1: inf, 2: pst, 3: lat, 4: ant, 5: sp, and 6: asp. Therefore, DI values are calculated for a total of 15 pairs of two different local regions, that is, 1-2, 1-3, 1-4, . . . , 5-6. According to the definition of a DI value in this embodiment, as the degree of dissynchrony increases, the DI value increases. Therefore, a search is made for a pair exhibiting the maximum DI value. In each application example, the obtained maximum DI value is displayed together with a conventional peak time difference as one preferred display form.

APPLICATION EXAMPLE 1

FIG. 4 is a view showing an example of how this dissynchrony evaluation support function is applied to a case of left bundle branch block for which CRT is effective. As a wall motion parameter, Radial-Strain as a wall motion parameter associated with a change in the wall thickening direction is used. As is obvious from FIG. 4, the maximum peak time difference is 414 [msec] between region "asp" and region "inf", whereas the DI value written as the maximum area difference time is 997 [msec] between region "asp" and region "lat". In addition, region "asp" and region "lat" are labeled by being displayed in color ellipses on the image.

Observing the dissynchrony evaluation support information provided in this manner allows the operator to easily and quickly comprehend from the results in the graph that region "asp" contracts early, and region "lat" has the maximum dissynchrony. Obviously, in addition, the degree of this dissynchrony is expressed larger than the conventional peak time difference. The operator can also easily visually recognize these regions on the ultrasonic image. It is said that in CRT, it is effective to place a pacing lead on the left ventricle side in a region exhibiting the maximum dissynchrony. It is therefore possible to comprehend the information of a position where the pacing lead should be placed as well as the degree of dissynchrony using DI values.

APPLICATION EXAMPLE 2

FIG. 5 is a view showing an example of how this dissynchrony evaluation support function is applied to a normal case. As a wall motion parameter, Radial-Strain as a wall motion parameter associated with a change in the wall thickening direction is used. The maximum peak time difference is 70 [msec] between region 1 and region 5, and the maximum barycentric time difference is 86 [msec] between region 1 and region 4, whereas the DI value written as the maximum area difference time is 72 [msec] between region 2 and region 5.

In addition, in this application example, the explanatory notes of local regions 2 and 5 are displayed in color ellipses on the graph, and the corresponding waveforms are labeled by being highlighted. DI values have degrees similar to those of conventional indices. In addition, the above example of the results on the case of left bundle branch block indicates that these indices are indices of dissynchrony with higher sensitivity than conventional indices.

APPLICATION EXAMPLE 3

FIG. 6 is a view showing another example of how this dissynchrony evaluation support function is applied to a normal case. As a wall motion parameter, Circumferential-Strain as a wall motion parameter associated with a change in the circumferential direction is used. The maximum peak time difference is 94 [msec] between region 3 and region 5, and the maximum barycentric time difference is 87 [msec] between region 3 and region 4, whereas the DI value written as the maximum area difference time is 75 [msec] between region 3 and region 6.

In this application example, the explanatory notes of local regions 3 and 6 are displayed in color ellipses on the graph, and the corresponding waveforms are labeled by being highlighted. DI values have degrees similar to those of conventional indices, and are minimum. This case indicates that these indices are indices of dissynchrony with higher specificity than conventional indices.

(Modification)

Figure 7:
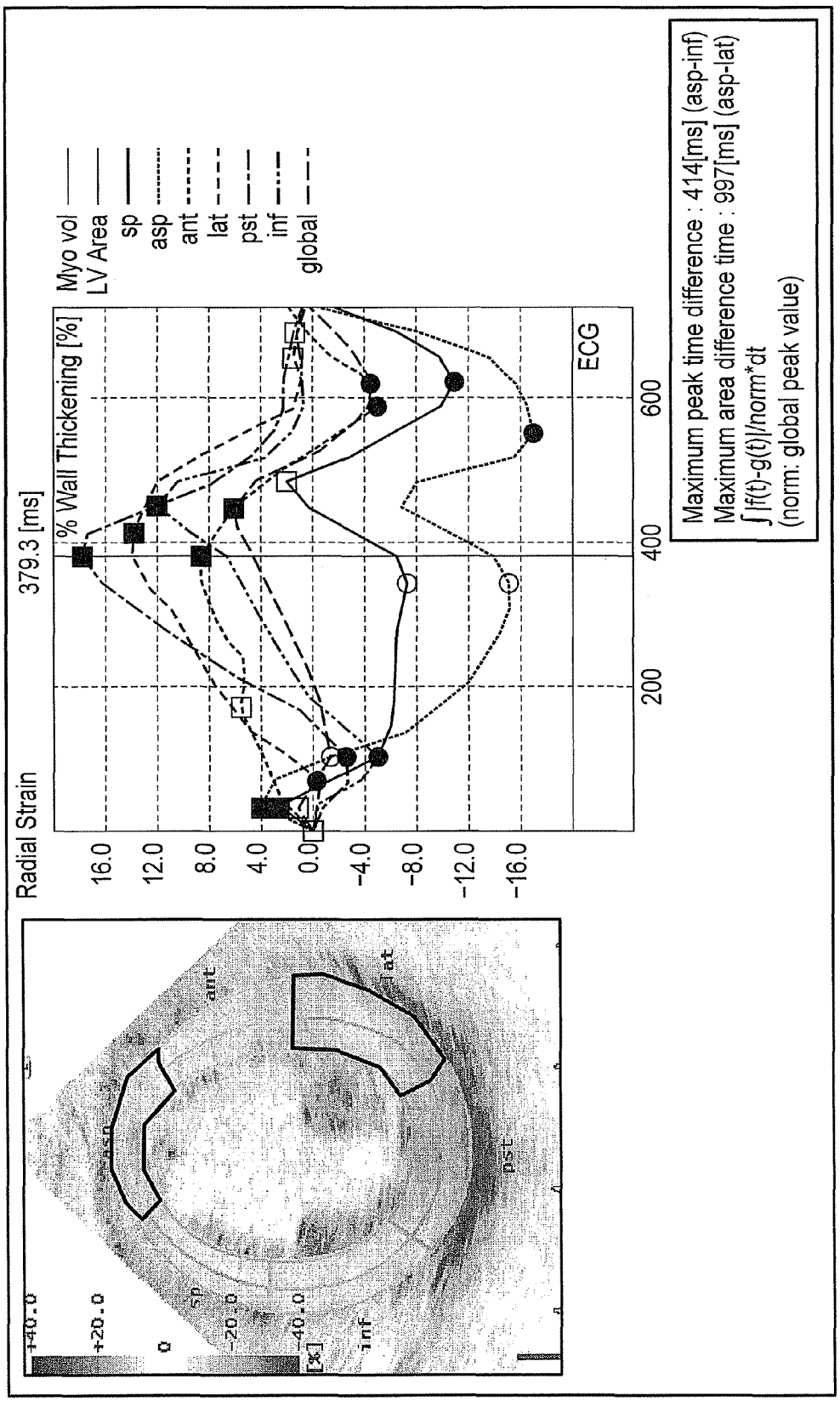
FIG. 7 is a view showing another example of the display form of dissynchrony evaluation support information.

FIG. 7 is a view showing an example of changing the manner of displaying a region from which the maximum DI value is obtained, with respect to, for example, the dissynchrony evaluation support information shown in FIG. 4. According to the dissynchrony evaluation support information displayed according to this example, 997 [ms] is obtained as the maximum DI value between region "asp" and region "lat", and the positions of region "asp" and region "lat" are displayed while being labeled by highlighted frame lines on the image.

This ultrasonic diagnostic apparatus calculates, as an index reflecting the discoordination of the left ventricle, a DI value obtained by normalizing the area difference value between two different regions of the heart by a predetermined value for all the combinations of two different regions (local regions) of the heart, and determines the maximum DI value among the calculated DI values. Since it is thought that the area difference value as a wall motion parameter between local regions reflects the discoordination of the left ventricle, the obtained maximum DI value can be an index reflecting the dissynchrony of the left ventricle. Using this DI index, therefore, can cover all types of dissynchrony useful for the determination of the application of CRT, and hence can implement CRT application determination with higher accuracy than dissynchrony evaluation with conventional indices.

In addition, this ultrasonic diagnostic apparatus displays, together with the obtained maximum DI value, a wall motion parameter image which labels at least one of two local regions corresponding to the maximum DI value, and temporal change curves, for dissynchrony evaluation support, in predetermined forms. Observing the displayed dissynchrony evaluation support information, therefore, allows the operator to visually recognize, easily and quickly, which two local regions of the heart have the maximum dissynchrony. In addition, displaying the maximum peak time difference and the like in addition to the above information, as needed, allows to visually recognize many pieces of diagnostic information at once, and hence can implement ultrasonic image diagnosis with a higher degree of freedom.

(Second Embodiment)

An ultrasonic diagnostic apparatus according to the second embodiment will be described next.

The first embodiment is configured to calculate DI values for all the combinations of two different local regions and to generate and display dissynchrony evaluation support information by using the maximum DI value among the calculated DI values. In contrast to this, the ultrasonic diagnostic apparatus according to this embodiment calculates a DI value for two arbitrary different local regions selected by the operator, and generates and displays dissynchrony evaluation support information by using the calculated DI value.

Figure 8:
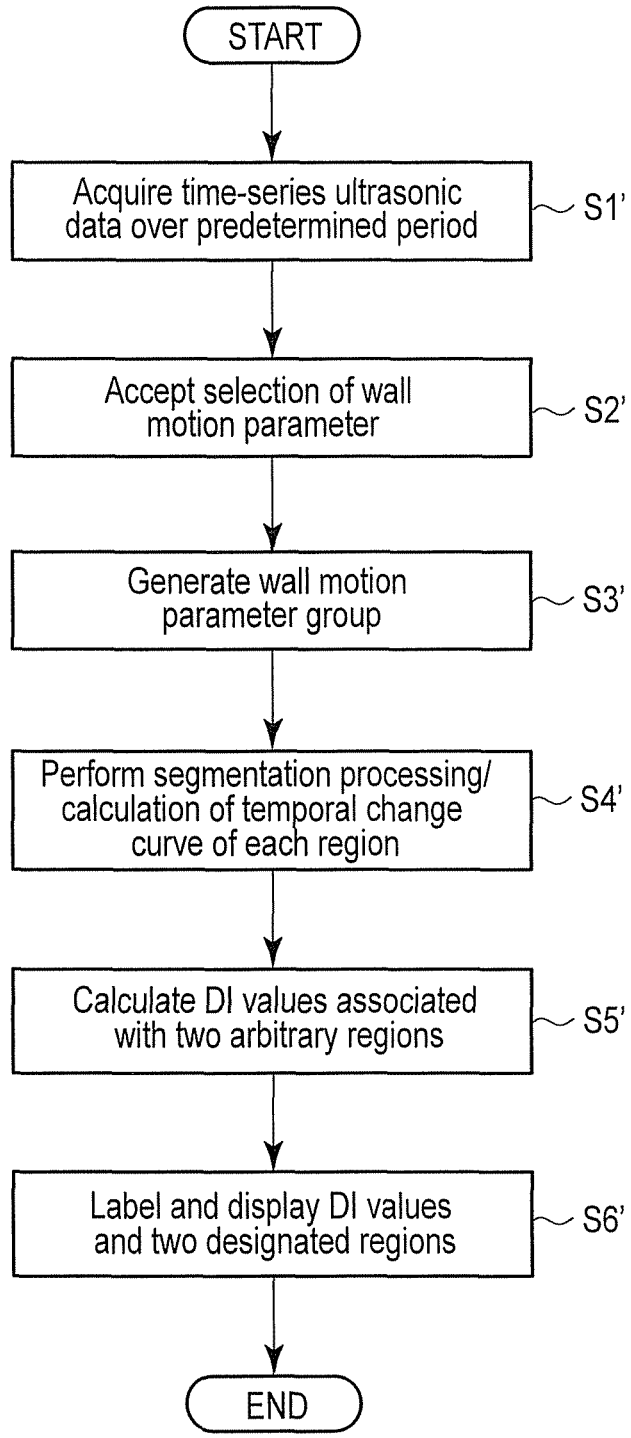
FIG. 8 is a flowchart showing a procedure for dissynchrony evaluation support processing according to the second embodiment.

FIG. 8 is a flowchart showing a procedure for dissynchrony evaluation support processing according to the second embodiment. Processing in steps S1' to S4' in FIG. 8 is essentially the same as that in steps S1 to S4 in FIG. 3. The contents of processing in steps S5' and S6' will be described below.

[Calculation of DI Value Associated with Two Arbitrary Regions: Step S5']

A control unit 31 receives the designation of two arbitrary regions from the operator via an operation unit 41. The designation technique to be used is not specifically limited. For example, it is possible to use a technique of designating two desired regions on a wall motion parameter image or ultrasonic image segmented into regions or designating two temporal change curves corresponding to desired two regions of temporal change curves corresponding to the respective regions. A DI value calculation unit 38 calculates a DI value associated with the two designated regions (step S5'). It is possible to use the same calculation technique as that described in the first embodiment.

[Labeling/Display of DI Value and Two Designated Regions: Step S6']

The display unit 23 displays a wall motion parameter image which labels at least one of the two designated local regions and temporal change curves, for dissynchrony evaluation support, together with the maximum DI value, in predetermined forms (step S6').

The ultrasonic diagnostic apparatus described above calculates, as an index reflecting the discoordination of the left ventricle, a DI value obtained by normalizing the area difference value between two different regions of the heart by a predetermined value for two desired regions (local regions). The apparatus can display, together with the obtained DI value associated with the two arbitrary regions and the maximum DI value, a wall motion parameter image which labels at least one of the two local regions and temporal change curves for dissynchrony evaluation support in predetermined forms.

Note that the present ultrasonic diagnostic apparatus is not limited to the above embodiments, and constituent elements can be variously modified and embodied at the execution stage within the spirit and scope of the embodiment. The following are concrete modifications.

(1) Each function associated with each embodiment can also be implemented by installing programs for executing the corresponding processing in a computer such as a workstation and expanding them in a memory. In this case, the programs which can cause the computer to execute the corresponding techniques can be distributed by being stored in recording media such as magnetic disks (floppy® disks, hard disks, and the like), optical disks (CD-ROMs, DVDs, and the like), and semiconductor memories.

(2) Each embodiment described above has exemplified the case in which ultrasonic data associated with the cardiac tissue is acquired by B-mode imaging. However, the present ultrasonic diagnostic apparatus is not limited to this, and ultrasonic data associated with the cardiac tissue may be acquired by the tissue Doppler method.

Various inventions can be formed by proper combinations of a plurality of constituent elements disclosed in the above embodiments. For example, several constituent elements may be omitted from all the constituent elements in each embodiment. In addition, constituent elements of the different embodiments may be combined as needed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
a probe configured to ultrasonically scan a two-dimensional region or a three-dimensional region as a region to be scanned which includes at least part of a heart of an object and acquire ultrasonic data associated with the region to be scanned;
motion vector processing circuitry configured to acquire temporal change curves of a wall motion parameter associated with a plurality of regions of the heart by using the ultrasonic data associated with the region to be scanned;
wall motion parameter processing circuitry configured to acquire an index value associated with cardiac wall motion by calculating an absolute value of a difference of the wall motion parameter of two arbitrary regions, of the plurality of regions of the heart, at each phase in an analysis period by using temporal change curves associated with the two arbitrary regions, calculating a total sum of the absolute values in the analysis period, and normalizing the total sum with a predetermined value; and
a display configured to display the index value in a predetermined form.

2. The apparatus of claim 1, wherein the wall motion parameter processing circuitry calculates the index values associated with all combinations of two regions selected from the plurality of regions and decides a representative value among the plurality of index values associated with all the combinations, and
the display displays the representative value and at least one of two regions from which the representative value is obtained.

3. The apparatus of claim 2, wherein the representative value is a maximum value of the index value.

4. The apparatus of claim 1, wherein the motion vector processing circuitry acquires an average temporal change curve using the respective temporal change curves associated with the plurality of regions, and
the wall motion parameter processing circuitry executes the normalization by using, as the predetermined value, a peak value of the average temporal change curve in the analysis period.

5. The apparatus of claim 1, wherein the wall motion parameter processing circuitry executes the normalization by using, as the predetermined value, a peak value of the temporal change curve associated with one of the two regions in the analysis period.

6. The apparatus of claim 1, wherein the analysis period is one of one cardiac cycle, a systolic phase, and a diastolic phase.

7. The apparatus of claim 1, further comprising an operation device configured to select one of a strain, strain rate, displacement, velocity, torsion, torsion rate, local area change and local area change rate as the wall motion parameter,
wherein the motion vector processing circuitry acquires a temporal change curve of the selected one of the wall motion parameters.

8. The apparatus of claim 1, wherein the wall motion parameter processing circuitry executes the normalization by using a predetermined value which is configured to be set for said each wall motion parameter.

9. The apparatus of claim 1, wherein the wall motion parameter processing circuitry acquires the index value having a temporal dimension unit.

10. An ultrasonic image processing apparatus comprising:
a motion vector processing circuitry configured to acquire temporal change curves of a wall motion parameter associated with a plurality of regions of a heart of an object by using ultrasonic data associated with a two-dimensional region or a three-dimensional region as a region to be scanned which includes at least part of the heart, which is acquired by ultrasonically scanning the region to be scanned;
a wall motion parameter processing circuitry configured to acquire an index value associated with cardiac wall motion by calculating an absolute value of a difference of the wall motion parameter of two arbitrary regions, of the plurality of regions of the heart, at each phase in an analysis period by using temporal change curves associated with the two arbitrary regions, calculating a total sum of the absolute values in the analysis period, and normalizing the total sum with a predetermined value; and
a display configured to display the index value in a predetermined form.

11. The apparatus of claim 10, wherein the wall motion parameter processing circuitry calculates the index values associated with all combinations of two regions selected from the plurality of regions and decides a representative value among the plurality of index values associated with all the combinations, and
the display displays the representative value and at least one of two regions from which the representative value is obtained.

12. The apparatus of claim 11, wherein the representative value is a maximum value of the index value.

13. The apparatus of claim 10, wherein the motion vector processing circuitry acquires an average temporal change curve using the respective temporal change curves associated with the plurality of regions, and
the wall motion parameter processing circuitry executes the normalization by using, as the predetermined value, a peak value of the average temporal change curve in the analysis period.

14. The apparatus of claim 10, wherein the wall motion parameter processing circuitry executes the normalization by using, as the predetermined value, a peak value of the temporal change curve associated with one of the two regions in the analysis period.

15. The apparatus of claim 10, wherein the analysis period is one of one cardiac cycle, a systolic phase, and a diastolic phase.

16. The apparatus of claim 10, further comprising an operation device configured to select one of a strain, strain rate, displacement, velocity, torsion, torsion rate, local area change and local area change rate as the wall motion parameter,
wherein the motion vector processing circuitry acquires a temporal change curve of the selected one of the wall motion parameters.

17. The apparatus of claim 10, wherein the wall motion parameter processing circuitry executes the normalization by using a predetermined value which is configured to be set for said each wall motion parameter.

18. The apparatus of claim 10, wherein the wall motion parameter processing circuitry acquires the index value having a temporal dimension unit.

* * * * *